US00PP11178P

United States Patent [19]

Zary

[11] Patent Number: Plant 11,178

[45] Date of Patent: Jan. 11, 2000

[54] SHRUB ROSE PLANT NAMED 'JACHOOD'

[75] Inventor: Keith W. Zary, Thousand Oaks, Calif.

[73] Assignee: Bear Creek Gardens, Inc., Medford, Oreg.

[21] Appl. No.: 08/943,629

[22] Filed: Oct. 3, 1997

[51] Int. Cl.[7] ..... A01H 5/00

[52] U.S. Cl. ..... Plt./107

[58] Field of Search ..... Plt./1, 2, 5, 101, Plt./107, 109, 114

*Primary Examiner*—Howard J. Locker

*Attorney, Agent, or Firm*—Klarquist Sparkman Campbell Leigh & Whinston, LLP

[57] ABSTRACT

A shrub rose plant having resistance to powdery mildew; bright, glossy canes; vigorous growth; glossy, dark green foliage; excellent rooting ability from hardwood cuttings; and excellence as understock for tree roses.

1 Drawing Sheet

The present invention relates to a new and distinct variety of rose plant of the shrub class which was originated by me by crossing an unnamed seedling with the variety Apple Jack, not patented.

The primary objective of this breeding was to produce a new rose variety having the powdery mildew resistance and hardwood cutting rooting ability of the unnamed red flowered, once blooming shrub female parent combined with the vigor and upright growth of the pink flowered repeat blooming male shrub. The cross was designed to produce a new rootstock capable of replacing the variety Dr. Huey for use in tree rose production. The objective was substantially achieved, along with other desirable improvements, as evidenced by the following unique combination of characteristics that are outstanding in the new variety and that distinguish it from its parents, as well as from all other varieties of which I am aware:

1. Resistant to powdery mildew;
2. Bright green, glossy canes;
3. Extremely vigorous, upright growth;
4. Glossy, dark green foliage;
5. Excellent rooting ability from hardwood cuttings.

JAChood has proved to be a reliable tree rose stock in the production of 18", 24" and 36" tree roses. The long canes root well as hardwood cuttings; they accept buds of many different scions tested; they store well as dormant tree roses in cold storage; they keep their attractive smooth bark; and their vigor produces large, robust plants.

Asexual reproduction of this new variety by hardwood cutting propagation, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Unnamed seedling.

*Pollen parent.*—Apple Jack (not patented).

Classification:

*Botanical.*—Rosa hybrida.

*Commercial.*—Shrub.

FLOWER

Observations made from specimens grown in a field environment at Wasco, Calif., from January, 1933 to March, 1997.

Blooming habit: Spring only, on 2 year or older wood.

Bud:

*Size.*—¾" long when the petals start to unfurl.

*Form.*—The bud form is short, pointed ovoid.

*Color.*—When sepals first divide, bud color is Red Group 52C. When half blown, the upper sides of the petals are Red Group 52D; and the lower sides of the petals are Red Group 52D.

*Sepals.*—Color: Green group 138B. Surface texture: Covered in fine hairs. There are three lightly appendaged sepals. There are two unappendaged sepals with hairy edges.

*Receptacle.*—Color: Green Group 139B. Shape: Apple. Size: Small, (3/16" long×3/16" wide). Surface: Glandular.

*Peduncle.*—Length: Short (1½"). Surface: Glandular. Color: Green Group 137B, but when exposed to bright sun acquires a bronze cast (Greyed Red 178A). Strength: Erect.

Bloom:

*Size.*—Small. Average open size is two inches.

*Borne.*—Several together and in rounded clusters of three to seven flowers.

*Stems.*—Very long (6' to 10'). Strong.

*Form.*—When first open: High centered. Permanence: Flattens; outer petal edges curl slightly.

*Petalage.*—Number of petals under normal conditions: 25–30.

*Color.*—The upper sides of the petals are Red Group 52D. The reverse sides of the petals are Red-Group 52D. The base of the petals is a small, white, half moon (1/16"×1/16") at the point of attachment. The major color on the upper side is Red Group 52D.

*Variegations.*—White (White Group 155D) streak present on upper surface of many petals.

*Discoloration.*—The general tonality at the end of the first day: No change. At the end of the third day: Fading in bright sun to Red Group 55D.

*Fragrance.*—Moderate.

Petals:

*Texture.*—Thin.

*Shape.*—Deltoid.

*Form.*—Tips slightly recurved.

*Arrangement.*—Imbricated, with a few petaloids in the center.

*Persistence.*—Hang on and dry.

*Lastingness.*—On the plant: Short (3–4 days). As a cut flower: Not tested.

Reproductive Parts:

*Anthers.*—Size: Medium. Quantity: Many. Color: Yellow. Arrangement: Regular around styles; mixed with petaloids.

*Filaments.*—Color: Yellow, with some red.

*Pollen.*—Color: Lemon yellow.

*Styles.*—Color: Reddish pink.

*Stigmas.*—Color: Greenish white.

Plant:

*Form.*—Shrub.

*Growth.*—Very vigorous; upright. This shrub is extremely vigorous, growing to over 10-feet in height and 8 feet in spread in one growing season in Wasco, Calif. Plants grow upright with strong, rigid, thick canes and do not require support.

*Foliage.*—Number of leaflets on normal mid-stem leaves: 7.

*Size.*—Large (5½"×3").

*Quantity.*—Abundant.

*Color.*—New foliage: Green Group 137C with a blush or cast of Greyed Orange Group 175A. Old foliage: Upper surface, Green Group 139A; lower surface, Green Group 139C.

*Shape.*—Broadly oval.

*Texture.*—Upper side: Leathery, glossy.

*Edge.*—Serrated.

*Serration.*—Single, small.

*Petiole rachis.*—Color: Reddish.

*Petiole underside.*—Rough, with prickles and glands.

*Stipules.*—Long (1"); serrated, bearded.

*Disease resistance.*—Resistant to mildew and rust under normal growing conditions at Wasco, Calif.

Wood:

*New wood.*—Color: Light green with a reddish case. Bark: Smooth.

*Old wood.*—Color: Green with glossy appearance. Bark: Smooth.

Prickles:

*Quantity.*—On main canes from base: Ordinary. On laterals from main canes: Ordinary.

*Form.*—Short (⅛" to 3⁄16"); hooked slightly by downward.

*Color when young.*—Red.

Small prickles:

*Quantity.*—On main stalks: None. On laterals: None.

I claim:

1. A new and distinct variety of rose plant of the shrub class, substantially as herein shown and described, characterized particularly as to novelty by its resistance to powdery mildew; its bright glossy canes; its extremely vigorous growth; its glossy, dark green foliage; its excellent rooting ability from hardwood cuttings; and the ability of its canes to serve as understock for tree roses.

* * * * *

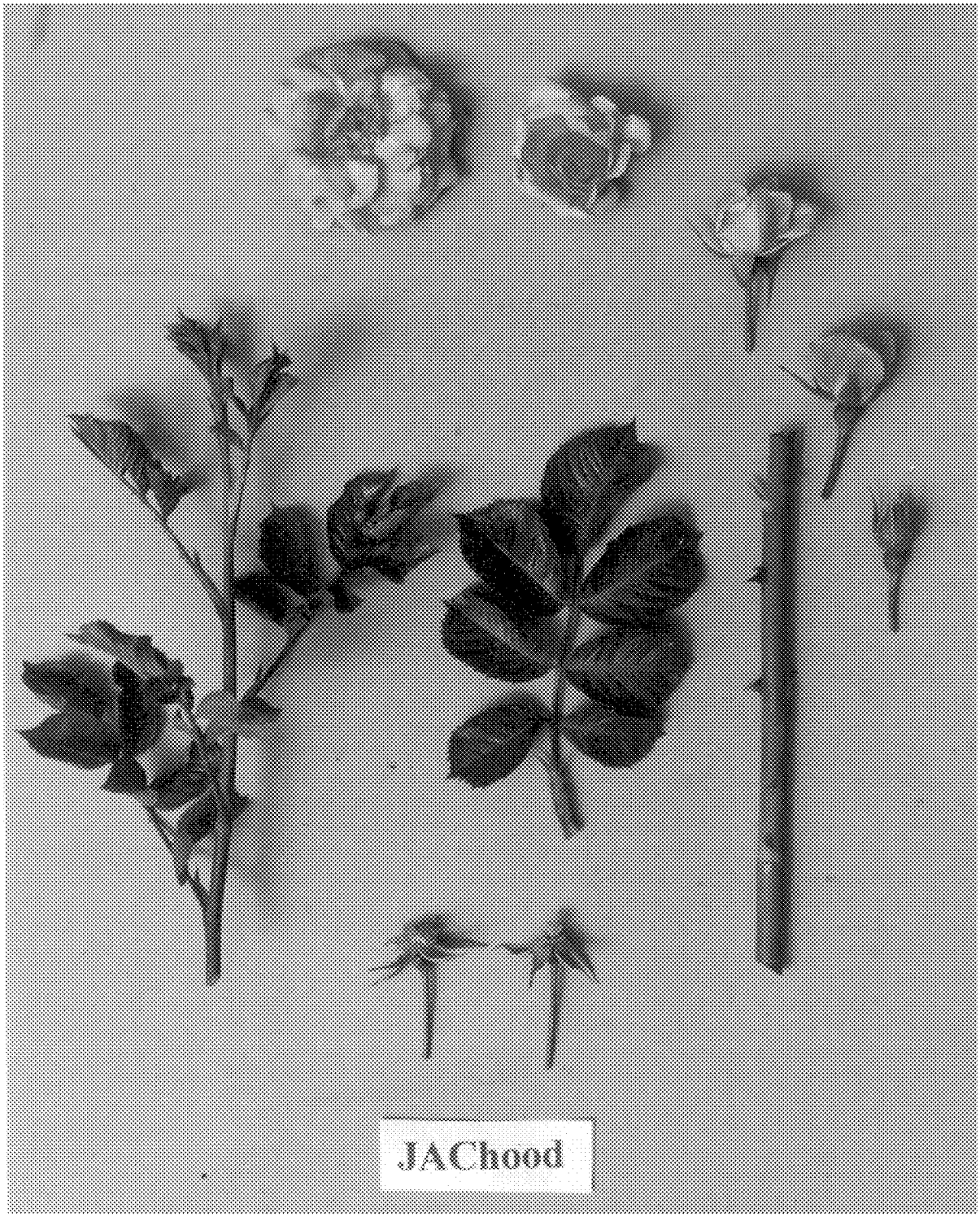
JAChood

UNITED STATES PATENT AND TRADEMARK OFFICE
CERTIFICATE OF CORRECTION

PATENT NO. : PP 11,178

DATED : January 11, 2,000

INVENTOR(S) : Keith W. Zary, Ph.D.

It is certified that errors appear in the above-identified patent and that said Letters Patent is hereby corrected as shown below:

In the Specification:

Col. 2, line 8, reads "January, 1933". It should read --January, 1993--.

Col. 4, line 11, reads " reddish case". It should read --reddish cast--.

Signed and Sealed this

Fifteenth Day of May, 2001

Nicholas P. Godici

*Attest:*

NICHOLAS P. GODICI

*Attesting Officer*

*Acting Director of the United States Patent and Trademark Office*